US010085668B2

(12) United States Patent
Jung (10) Patent No.: US 10,085,668 B2
(45) Date of Patent: *Oct. 2, 2018

(54) EEG HAIR BAND

(71) Applicant: NGOGGLE INC., San Diego, CA (US)

(72) Inventor: Melody Jung, San Diego, CA (US)

(73) Assignee: NGOGGLE INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/376,382

(22) Filed: Dec. 12, 2016

(65) Prior Publication Data

US 2017/0150925 A1   Jun. 1, 2017

Related U.S. Application Data

(63) Continuation of application No. 13/899,515, filed on May 21, 2013, now Pat. No. 9,517,031.

(60) Provisional application No. 61/649,519, filed on May 21, 2012.

(51) Int. Cl.

| *A61B 5/0478* | (2006.01) |
|---|---|
| *A61B 5/00* | (2006.01) |
| *A61B 5/04* | (2006.01) |
| *A45D 8/36* | (2006.01) |
| *A45D 8/24* | (2006.01) |
| *A45D 8/30* | (2006.01) |
| *A45D 8/00* | (2006.01) |

(52) U.S. Cl.
CPC .......... *A61B 5/0478* (2013.01); *A61B 5/0006* (2013.01); *A61B 5/04012* (2013.01); *A61B 5/6803* (2013.01); *A45D 8/24* (2013.01); *A45D 8/30* (2013.01); *A45D 8/36* (2013.01); *A45D 2008/004* (2013.01)

(58) Field of Classification Search
CPC ............................ A61B 5/0478; A61B 5/6803
See application file for complete search history.

(56) References Cited

U.S. PATENT DOCUMENTS 9,517,031 B2 * 12/2016 Jung .................... A61B 5/6803
2012/0190959 A1   7/2012 Hayakawa et al.

FOREIGN PATENT DOCUMENTS

WO   WO 2011/002093   1/2011

* cited by examiner

*Primary Examiner* — Lee S Cohen
(74) *Attorney, Agent, or Firm* — Knobbe Martens Olson & Bear LLP (57) ABSTRACT

The present invention relates to hair band EEGs. More particularly, the present invention relates to hair bands.

19 Claims, 10 Drawing Sheets

EEG HAIR BAND

CROSS REFERENCE TO RELATED APPLICATIONS

This application is a continuation of U.S. patent application Ser. No. 13/899,515, now issued U.S. Pat. No. 9,517,031, filed on May 21, 2013, which claims priority under 35 U.S.C. § 119(e) to U.S. Provisional Application No. 61/649,519, filed May 21, 2012, the contents of which are all hereby incorporated by reference in their entireties.

FIELD OF THE INVENTION

The present invention relates to EEG hair band. More particularly, the present invention relates to hair bands that record electroencephalograph signals.

BACKGROUND OF THE INVENTION

An electrode system to capture bioelectric signals, such as electroencephalograph (EEG) signals, from a subject generally should address various requirements including safety needs, cost, power consumption, performance, ease-of-use, appearance and subject comfort. In a non-clinical application the relative importance of these factors may be somewhat different to that in a clinical application. In a clinical application, for example, a relatively skilled technician applies the electrodes, whereas in non-clinical application, the electrodes are more likely to be applied by a person with no training or knowledge of correct application or placement of the electrodes. Convenience and subject comfort are also generally more important in a non-clinical application. A patient in a clinical situation is more likely to be tolerant of some level of discomfort or inconvenience when testing and calibrating electrodes than a person in a non-clinical setting that may need monitoring over long periods of time, without interfering with the patient's daily routines.

Conventional EEG systems use scalp level electrode attachment to monitor neurological activity. Conductive gels and pastes are often applied before placement of the scalp electrodes to improve sensitivity. However, application of conductive gels and pastes is often inconvenient and time consuming. Furthermore, conductive gels and pastes can often bleed between neighboring electrodes and cause signal contamination.

There are number of hats, helmets, and headgear that have been developed to collect EEG data without the use of collodion. However, these devices still require the assistance of a technician. Many devices are only good inside a clinic or a doctor's office and impractical for use during everyday living. There have been devices that measure EEG outside of a clinic or doctor's office, but those devises tend to be large and hard to disguise when wearing the devise and going about one's daily activity.

Some efforts have been made in the development of dry electrodes. However, available dry electrodes have a variety of limitations, including movement and interference, particularly from hair. Consequently, it is desirable to provide improved electrodes for EEG.

SUMMARY OF THE INVENTION

The present disclosure is directed to medical hair accessories, particularly a hair fastening EEG. The hair band includes a head band or hair clip and one or more EEG teeth. The invention device has a generally arcuate shape with opposed free ends and is adapted for positioning EEG teeth on the scalp of a wearer's head secured by the hair of an individual. The invention can be shaped generally to circumnavigate the head of an individual traveling from near one ear to traveling near the other ear of an individual retained by the force of the head band against the head. Similarly, but smaller, the hair clip is a device that generally clips to an individuals hair to position one or more electrodes to the scalp of the individual, but is made stationary by fastening a bundle of hair near the scalp of an individual's scalp. The teeth comprises contacts positionable against the wearer's head, an inner and outer member to secure the hair and minimize movement of the contact on the scalp of the wearer.

BRIEF DESCRIPTION OF THE DRAWINGS

Embodiments of the present disclosure will be better appreciated by reference to the drawings wherein:

FIGS. 4A-4C are multi-perspective views of the barrette of the present disclosure (separate of the hair band). FIG. 4C is a perspective view of a barrette;

DETAILED DESCRIPTION

The present disclosure is directed to a electroencephalogram (EEG) hair band or clip to measure brain electrical activity, comprising a hair band to hold and support a plurality of electrode hair clips in a configuration to acquire and monitor electroencephalogram (EEG) signals from the scalp. Embodiments of the present disclosure are illustrated in FIGS. 1-7.

Figure 1:
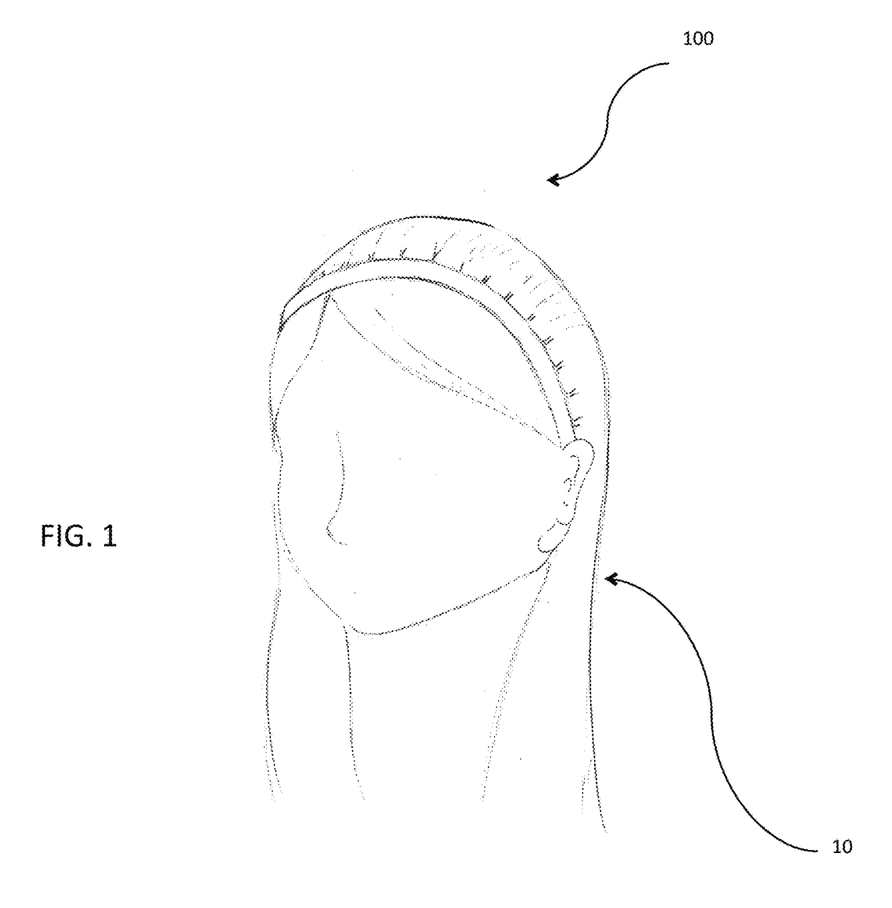
FIG. 1 is a perspective view of the hair band worn by a wearer.

FIG. 1 shows an embodiment of a portion of the device, a hair band, as it might appear fitted to a wearer's head, for example. The hair band 100 contains electrical components and structures encased in the hair band or in a hair band covering to protect the hair band components and provide a comfortable fit, while measuring electrical signals from the surface of the wearer's head 10. In a preferred embodiment, hair band 100 is adapted and configured for positioning about a wearer's head 10, e.g., along the crown of the head. Hair band 100 may define a generally arcuate configuration, such as a c-shape, u-shape, or horseshoe-shape. Other shapes are also envisioned to those skilled in the art, such as rectangular, circular, and the like.

The hair bands 100 described above may be fabricated from suitable rigid or flexible material. In embodiments, the hair bands may be made from a polymeric material manufactured via known injection molding techniques. Such hair bands may be adapted to flex outwardly whereby the free ends may be displaced from an unbiased position to a biased position to fit about the wearer's head. Alternatively, the hair bands may also be fabricated from a fabric, metal, or combinations thereof. Hair band preferably may be ornamental or fashioned to be worn in public, for example, may have material that may have a woven, braided, or other ornamental design. Hair band may also have any color, texture, or pattern thereon. Hair band may also have accessories attached thereto, such as bows, jewels, and the like. Hair band may be of a height to lie flush with hair band. Additionally, a slightly flexibly material can be utilized to allow for variations in the size and shape of the wearer's size, e.g. children and adult. The hair band can further comprise a covering composed of elastomer material (silicone, urethane, etc.) that completely encapsulates electronics and the body and housing of the hair band, yet allows the hair band cover to be flexible so that the hair band can form a loop for fitting the head of the user.

Figure 8:
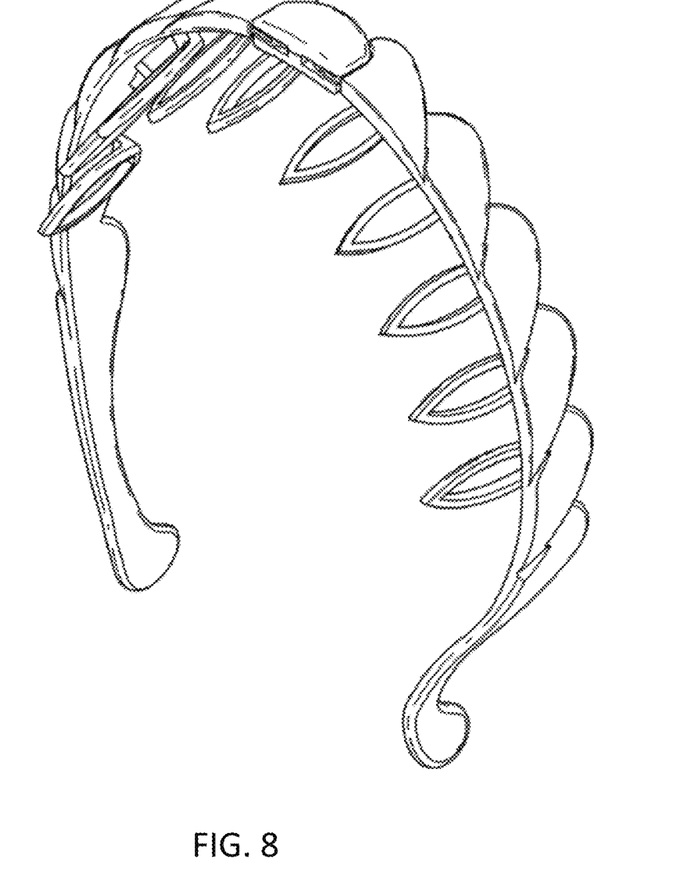
FIGS. 8-10 illustrate decorative designs of the present invention.
Figure 9:
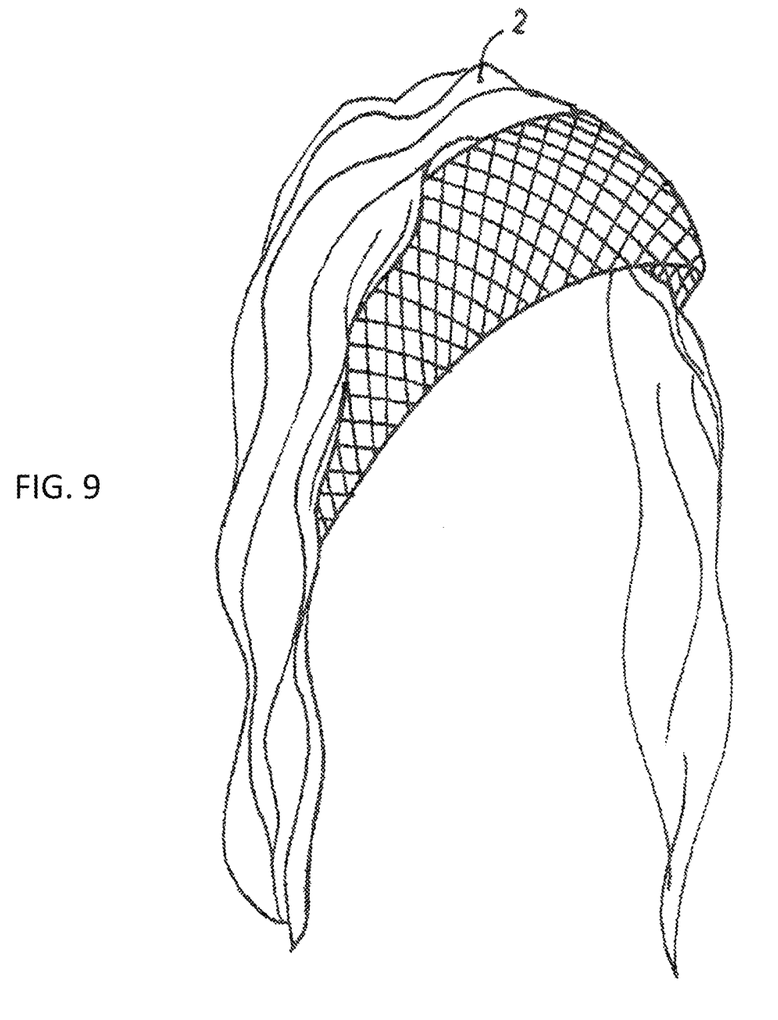
Figure 10:
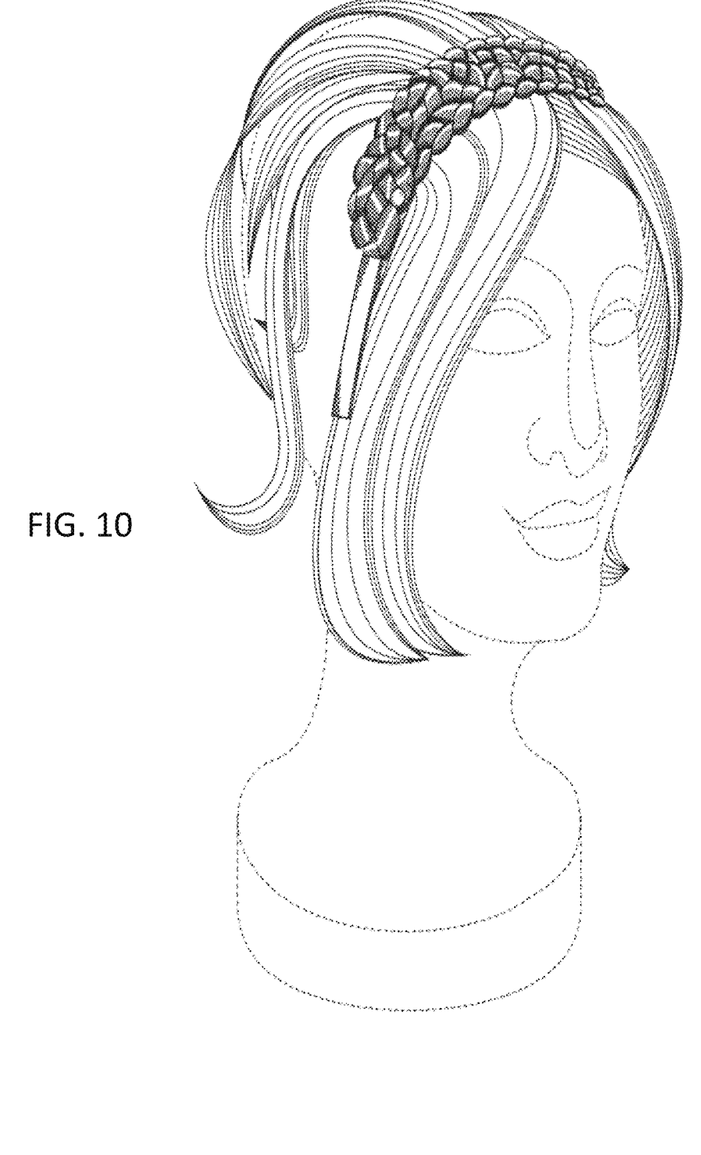

Hair band can be decorated with external decorations, e.g., flowers, fabric, design, or other fashionably or other decorative relevant designs and elements and materials to be more aesthetically pleasing, as shown in FIGS. 8, 9 and 10. In some embodiments, the body comprises one or more of a heart, insect, animal, flower, and other decorative shape. In further embodiments, the body comprises multiple designs. The discrete decorative elements may comprise anything which will decorate the wearer's hair and draw attention to the wearer. The decorative elements should be large enough to be noticeable but small enough to neither encumber the wearer nor to inhibit the appearance that they are independently attached to the wearer's hair. The decorative elements may be selected to cater to many styles, tastes and ages of wearer. For example, the decorative elements may include stones, gemstones, beads, miniatures, and miniature cartoon characters, figurines, letters, flowers, birds, insects and animals. They may be used on a variety of materials such as metal, stone, wood, or plastic, and maybe formed in a variety of colors. Mixtures of decorative elements either on different elongated members, or on the same member, may create particularly striking effects.

Figure 2:
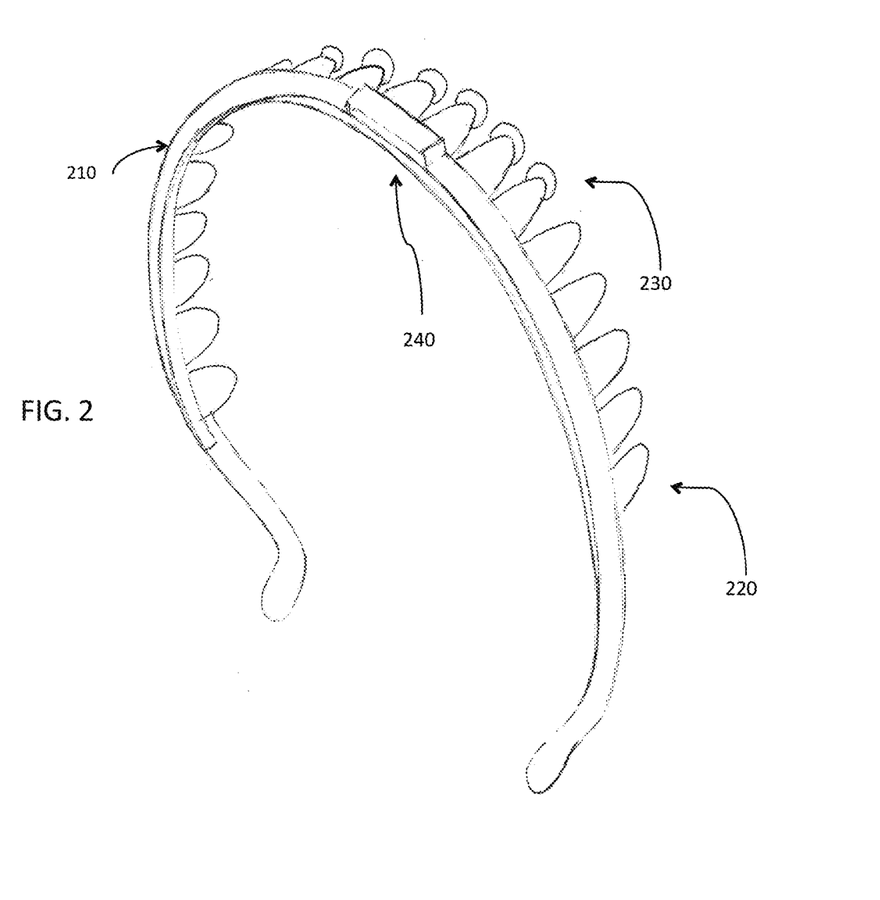
FIG. 2 is a side view of the hair band of the FIG. 1 of the present disclosure.

As shown in FIG. 2, hair band 210 includes a plurality of teeth or projecting members 220 to provide contact with the scalp of a subject. Teeth can circumnavigate hair band to record EEG signals across, for example, the top of the head from ear to ear. Multiple hair bands can be used to measure different cross sections of the head (see, e.g., FIG. 6). Teeth can be permanently attached to hair band or can be removable/replaceable, for example, plug-in sockets or male/female sockets. Teeth (singular tooth) 220 are of a sufficient length to be captured within strands of hair, where the tips of the teeth 230 are able to make contact with the scalp. Teeth can be placed in perpendicular to hair band, parallel with hair band, protruding from hair band, and the like. Teeth 220 are adapted to engage strands of hair to assist in retaining hair band 210 on the wearer's head. Teeth 220 may also assist in pulling hair away from the face of the wearer. Teeth 220 may have rounded outer surfaces to avoid trauma to the wearer's head, more preferably flanged tips to ensure safe consistent contact with scalp. Teeth 220 may be arranged about aperture or, alternatively, in one or more linear rows provided in spaced relation along hair band. The teeth 220 may be made of fabric, polymeric, or metal materials that may provide additional structure, stiffness, or flexibility to the hair band 210 to assist in placing the contacts 230 with the scalp of the user. The hair band 210 can house electronics 240 such as a battery and other electronic components (wireless transmitter, processor, etc.) engaged through the teeth 220 to the contacts 230, or, for example, at the ends 240 of the hair band 210.

Figure 3:
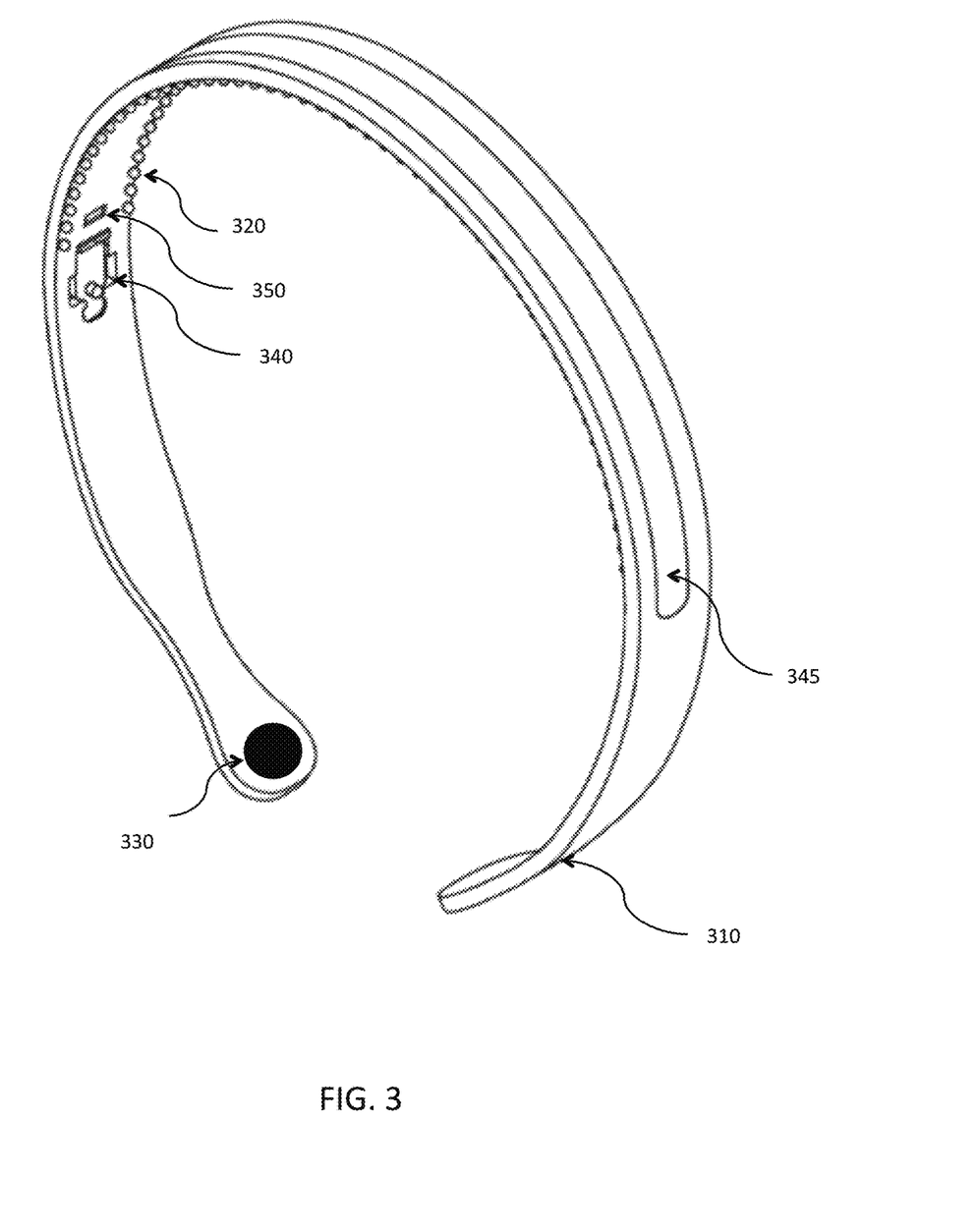
FIG. 3 is a side view of an alternate hair band of the present disclosure.

As shown in FIG. 3, hair band 310 can comprise small teeth 320 that may have contacts 320 to reach the scalp of the individual or have separate contacts 330 that are on the body of the hair band 310. The hair band can house electronics 340 such as a battery (preferably a replaceable battery in a battery compartment 340) and other electronic components (wireless transmitter, processor 350, etc.) engaged through the body 345 of the hair band.

Figures 4A, 4B:
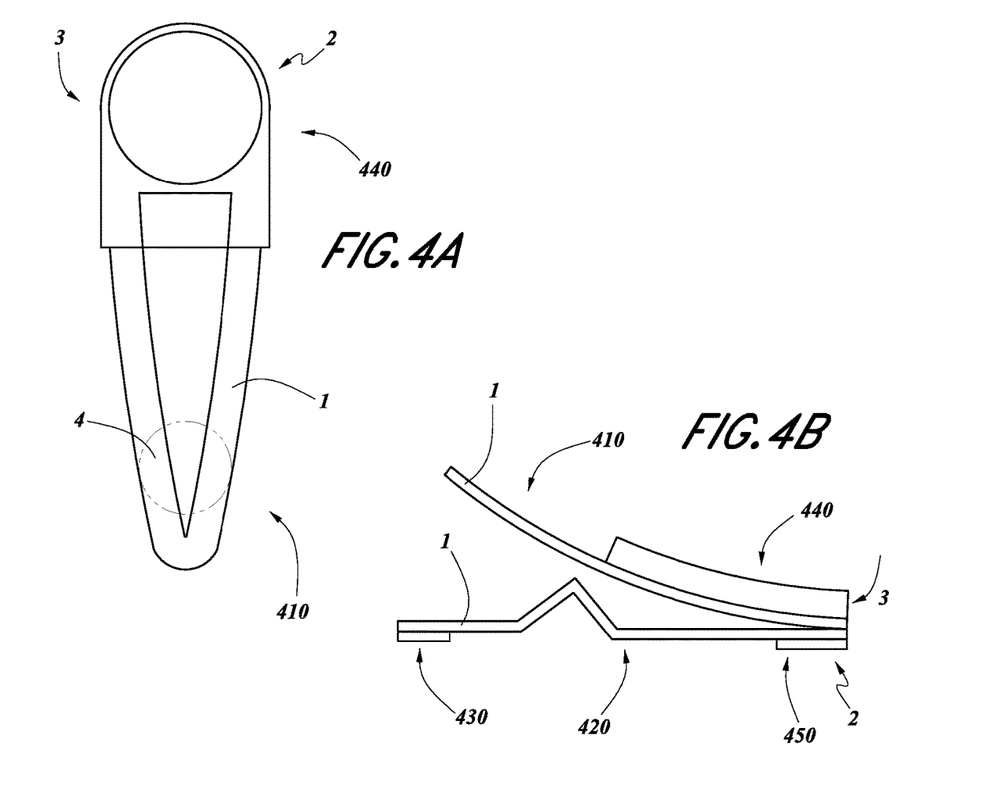
FIG. 4A schematically illustrates a top view of the outer locking member, battery, enclosure, and electrode of a barrette.
FIG. 4B is a side view of a barrette.
Figure 4C:
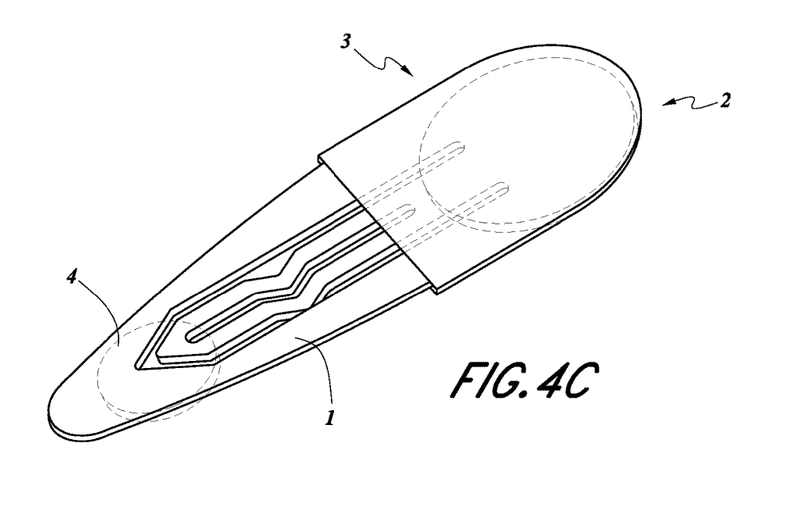

In one embodiment, the band can be one tooth as shown in FIGS. 4A-4C as a barrette (also known as a hair clip, hair-slide or bobby pin) comprising a locking member with two opposing parts, an outer locking member 410 and an inner support member 420, to engage the strands of hair to assist in retaining hair band on the wearer's head. This can be alternated with the locking member as the portion touching the scalp, i.e., internal, and the support member on the outside as the arcuate hair band. FIGS. 4A-4C show teeth integrated as part of the hair band, with the teeth comprising the inner support 420 and the locking member 410 hinged to one another for pivotal movement and can be locked in a closed position by a clasp. As such, this type of barrette is placed over the strands of hair such that the outer member 410 is the hair band outwardly exposed and the support member 420 is tucked underneath the strands of hair. The locking member 410 and inner support member 420 are then pivoted to a closed position such that the strands of hair are clamped between the inner retaining member 420 and the locking member 410. Accordingly, the outer member 410 is maintained in an outwardly facing direction, which can serve as a fashion item that enhances the appearance of the barrette and its user. More importantly, however the barrette is adapted to position the tip of the teeth 430 to contact the scalp of the wearer held in place by the locking mechanism of the barrette. In the more preferred embodiment, the two opposing parts are concave pieces, with the outer member 410 snapping between two concave orientations, opposing the inner member 420 and in parallel with the inner member 420. By having a locking member 410 that is concave, the tip 430 is oriented to be in contact with the scalp of the wearer, with the teeth engaged in this position by the hair of the wearer.

Figure 5:
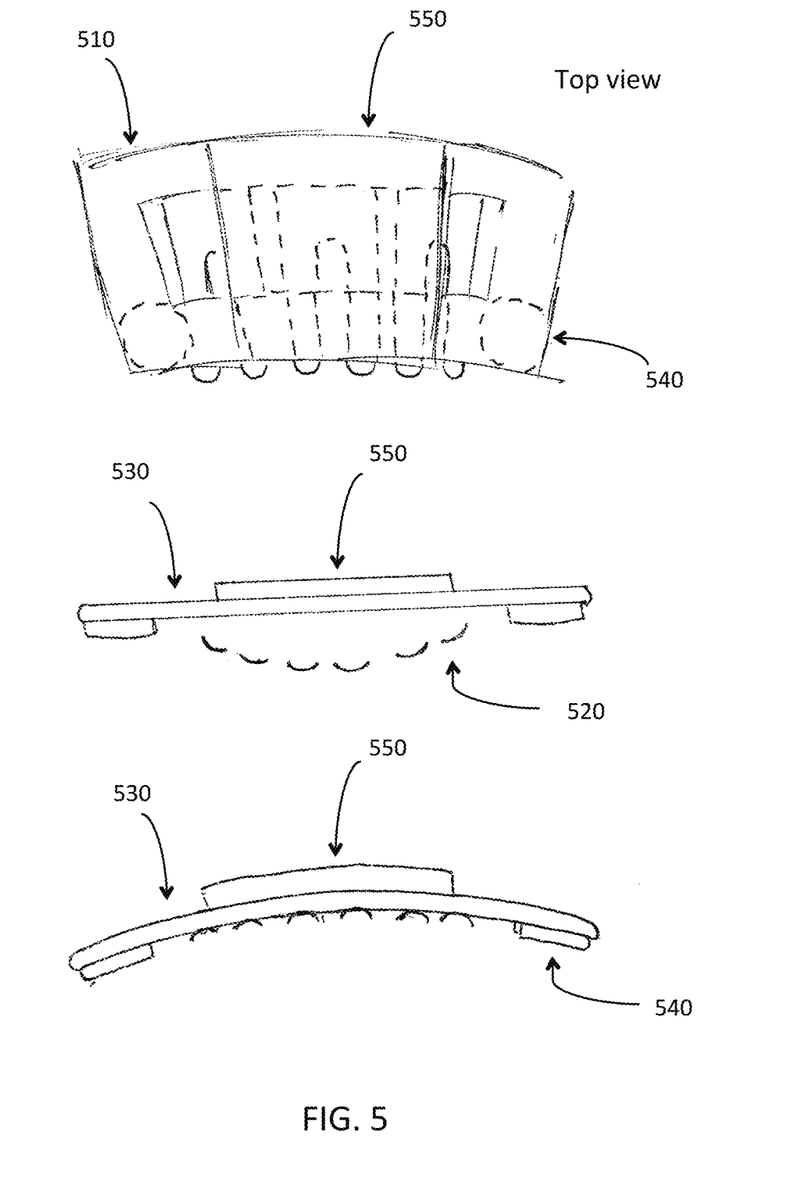
FIG. 5 is a multi-perspective view of the wig clip of the present disclosure (separate of the hair band and barrette)
Figure 6:
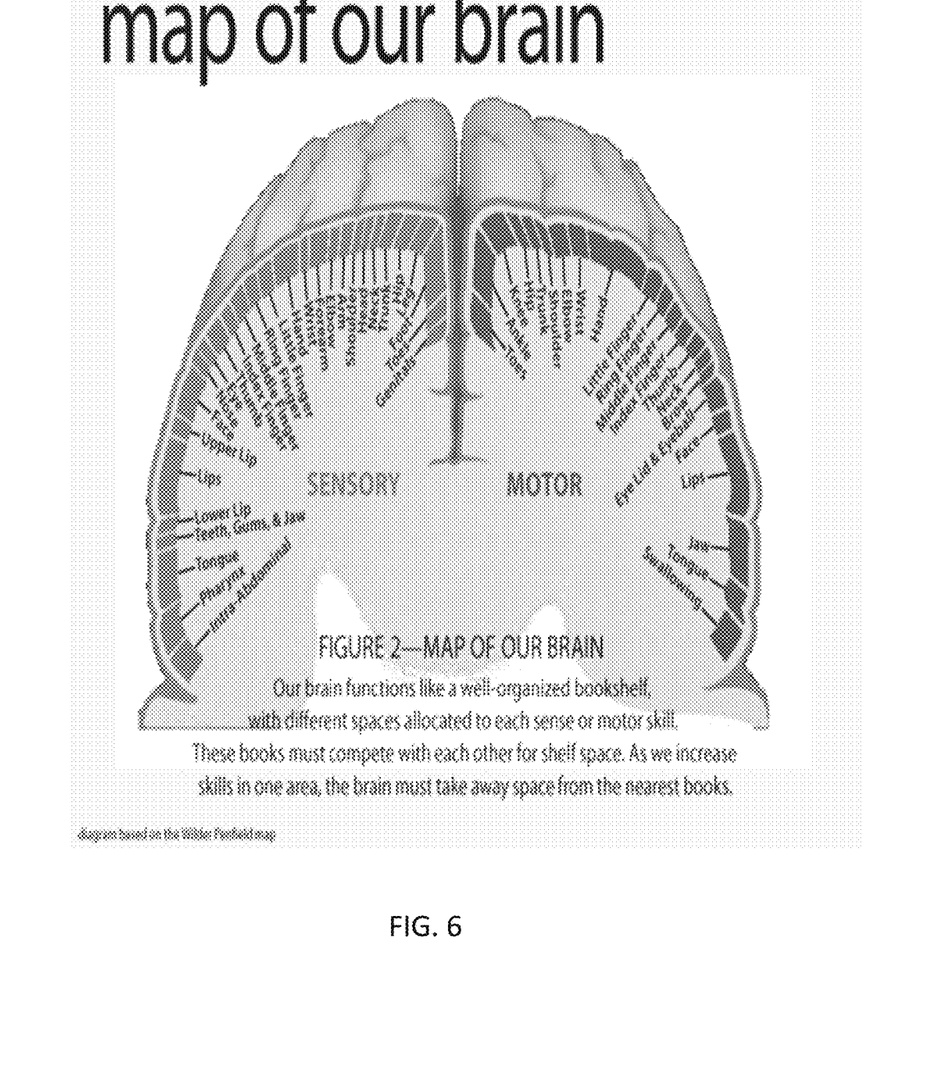
FIG. 6 is a map of the anatomical divisions of the primary motor cortex and the primary somatosensory cortex of the brain.

As shown in FIG. 5, multiple teeth can be attached to a barrette 510 that does not rely on circumnavigating the head but clips to a smaller portion of the head by securing to hair. The structure is similar to what is known in the art as toupee snap clip (also known as a wigs snap clip) 510, which comprises a locking member with two opposing parts, an inner locking member 520 and an outer support member 530, to engage the strands of hair to assist in retaining wigs band on the wearer's head. FIG. 5 shows teeth independent of wigs band in one embodiment. The locking member 520 and the support member 530 can be snapped and locked in a closed position (FIG. 5 bottom panel). As such, this type of snap clip is placed underneath the strands of hair. The support member 530 and locking member 520 are then pivoted to a closed position such that the strands of hair are clamped between the inner locking member 520 and the outer support member 530. Electrodes can be placed on the tips of each tooth, as discussed above, or alternatively, or in addition, the support member 530 lies flat on the scalp allowing electrodes 540 on the snap clip to contact the scalp of the wearer, while held tightly in place by the inner locking member 520. The snap clip can house electronics 550 such as a battery and other electronic components (wireless transmitter, processor, etc.)

One particular type of barrette includes a locking member, an inner retaining member and an outer support member with a decorative member secured thereto. Quite typically, the outer support member and the locking member are hinged to one another for pivotal movement and can be locked in a closed position by a clasp. In an alternate embodiment, the present invention is directed to a barrette (also known as a hair clip, hair-slide or bobby pin) EEG comprising a clasp or ping for holding an EEG contact in place against the scalp by pressing or clipping two pieces or metal, plastic or other material in parallel secured against hair.

Electrodes for contact with the skin can be placed on the band or clip itself or on the teeth. For example, electrodes can be placed on the tips of each band or clip that contacts the skin of the individual, such as the scalp or neck. More preferably, or in addition, electrodes are placed on each tooth that can be positioned to contact the skin of the patient. Electrode teeth can either be entirely conductive or have conductive tips to acquire the EEG signal. The electrode teeth point of contact with the scalp is the electrode contact that can be a component of the electrode teeth, integrated within the electrode teeth or the tip of the teeth itself. Although the electrode contacts can use wet electrodes (e.g., silver/silver chloride (Ag/AgCl) electrodes) that require skin preparation and application of conductive gels, it is preferred to have dry electrodes. Dry electrodes can have either a conductive or insulating contact material. In particular embodiments, a capacitive coupling between the scalp and the electrode is created so that the signal is transferred to the electrode by a capacitive conduction mechanism. Dry electrode sensor material may be a metal, preferably inert metals, like stainless steel, gold, silver (silver chloride), tin, palladium, and platinum or other conductive material to acquire an electrical signal. The electrode contact can be in any shape, including circular, square, triangular, or such other shape sufficient to make contact with the wearer's scalp.

The electrodes may be fabricated using semiconductor-manufacturing processes to provide individual electrode integrated circuits. According to various embodiments, each contact has a diameter of 0.1 mm-20 mm, more particularly 0.5 mm to about 10 mm. Similarly, the width and thickness of the contact can be in the same range as the width. Smaller contacts more easily navigate through hair to reach the scalp surface. However, too small a contact leads to irritation, and a small contact still does not guarantee that it will reach the scalp. Larger contacts are more comfortable and can provide more surface area for measurement, but can be limited in their ability to read a uniform signal. For example, a large surface contact may not measure a consistent signal due to hair and motion that decouples the contact from the skin surface.

Dry electrodes, however, have significantly higher skin electrode impedance. For dry electrodes to be effective, the techniques and mechanisms of the present invention contemplate mechanisms for compensating for the high impedance. Impedance may vary and/or fluctuate in regions having a significant number of hair follicles. Impedance may also change in region having high skin elasticity. Each electrode is provided with multiple contact points or contact pads, on individual teethe or redundant teeth. In particular embodiments, each electrode selects a locally optimal or preferred signal from the different signals received from the multiple contacts. In some examples, the preferred signal may be a signal having the most consistent and/or highest amplitude during a set of calibrations. According to various embodiments, the locally optimal or preferred signal is amplified and sent to a transmitter. A system also may select a regionally preferred signal from a group of electrodes. According to various embodiments, regionally optimal signals are selected from a group of locally optimal signals. Alternatively, it may be preferable to have multiple hair bands, each with one or multiple teeth to create an array of electrodes or alternatively, create redundancy to ensure capture of a clean signal. Each tooth, on one hair band or multiple hair band, can be placed at various points around the head.

Preferably, each contact is coated with a material to allow for easy navigation through hair while also resisting corrosion, and/or insulation to minimize signal contamination. For example, each contact is coated with one or more polymers or other insulator, or other material. For, example titanium oxide ($TiO_2$) is inert on most physiologic media and effectively resists corrosion. In other examples, silicon nitride ($Si_3N_4$) can also be used. Each contact may be connected to selection circuitry to allow an electrode, or a system, to select one or more preferred signals of the electrode. In some instances, no signal may be suitable. Individual electrode may also include filters, capacitors, diodes, power supplies, and amplifiers, and transmitters.

Figure 7:
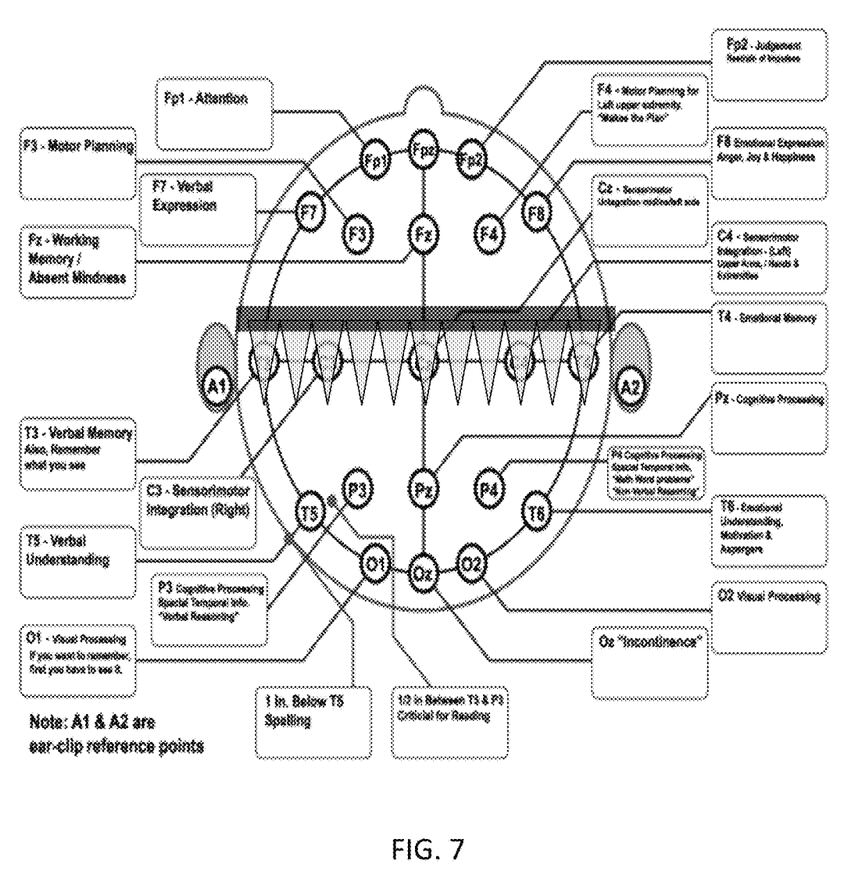
FIG. 7 is a positional drawing of the 10-20 system or International 10-20 system, an internationally recognized method to describe and apply the location of scalp electrodes in the context of an EEG test or experiment.

In a preferred embodiment hair band comprises an electrode assembly having an electrode connector with multiple electrode teeth emanating from the connector, and with each electrode tooth connecting to one or more individual electrodes (such as EEG electrodes, for example). The electrode assembly is preferably scaleable, allowing many different combinations and numbers of electrodes and electrode assemblies to be utilized. As to electrodes, the amount and arrangement thereof both can be varied corresponding to different demands. For example, as shown in FIG. 7, when being used in general EEG monitoring, it is common to use 16 channels, 32 channels or 64 channels acquisition; or when being used for approximately realizing the variation of brain waves only, the needed amount of electrodes becomes fewer, such as, typically, C3, C4, O1, O2 signals are needed in sleep study. Thus, there is no limitation. In addition, the most useful configuration will likely utilize one or more hair band connectors on the hair band. The electrode assembly typically will have more than one tooth, more preferably several or more electrode teeth each corresponding to an electrode lead, although different numbers of electrodes are easily supported, in the range of 2-300 or more electrodes, for example.

It is expected that one or more electrodes will be used as a ground terminal (that may be attached to the scalp, or alternatively to another part of the body, such as an ear, earlobe, or the chest, for example) for connection to the ground plane of the medical device. Further, one electrode is expected to be used as a reference electrode.

The EEG of the invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions. Each electrode is electrically connected to electronic circuitry that can be configured to receive signals from the electrodes and provide an output to a processor that can be mounted on the hair band or on a separate unit connected to the hair band. The electronic circuitry may also be configured to perform at least some processing of the signals received from the electrodes. In some implementations electronic circuitry can be mounted on or housed within the hair band. In a preferred embodiment, the EEG signal acquisition circuitry includes a processor, an analog signal processing unit, and an A/D (analog/digital) converter, but not limited, for example, filter and amplifier also can be included therein.

The invention hair band or clips may or may not contain any batteries or any other power supplies, which can be placed in the hair band (see, e.g., 240 in FIG. 2) or in each clip (see, e.g., 450 in FIGS. 4A-4C). If no batteries are included the device will be powered from the external receiving device via a cable. Power can be provided by an external recording device by a power supply or converter for input into a power conditioning and distribution circuit of the hair band. If wireless technology is implemented, the device should be self-powered via a battery.

The sparse electronics and small capacity battery can be fully covered or housed by an enclosure, which can be placed in the hair band (see, e.g., 240 in FIG. 2) or in each clip (see, e.g., 440 in FIGS. 4A-4C). The electrodes on the hair band can be individually electrically connected by conductive wires to EEG recorder that can be mounted on the device or mounted nearby for wired or wireless connection. For example, An EEG recorder can include an onboard recording device, such as a flash memory, or information can be transferred wirelessly from the EEG recorder assembly to the local user interface. Power consumption is obviously a concern for wireless transmission of information.

Preferably, in view of above, for reducing the wiring complexity, the electrical connection between modules can be located in the ear-worn structure, and/or a holding element, which is used to connect to both housings to assist in holding and supporting the ear-worn structure, and/or an electrode-positioning element, which is used to locate the position of electrode(s).

The data can be transmitted in any suitable manner. In one exemplary embodiment of the present invention, the medical device data is transmitted to the intermediary device using a wired connection, such as an RS-232 serial cable, USB connector, Firewire connector, or other suitable wired connection. A preferred form of carrying electrode wires is FPCB (flexible printed circuit board). FPCB is featured of flexible and capable of mounting electronic components, so that the functions of carrying electrode wires and fitting head's curve can be achieved at the same time, and further, because FPCB is also characteristic of lightweight, the FPCB-carried electrode wires can effectively reduce the weight added on user's head as compared with the traditional electrode wires. One kind of electrode FPCB starts from gathered multiple wires and gradually separates into respective electrode wires, and even through designing the shape of FPCB, an extendable function can be obtained additionally. Moreover, a further advantage can be obtained from FPCB-carried electrode wires, that is, since the electrode wires are integrated on FPCB, the movement of user will not change the relative distance among electrode wires, so that the interference between traditional electrode wires and the noises produced therefrom can be minimized.

Further preferably, the EEG signal acquisition circuitry also includes a RF module for performing wireless communication. In addition to off-line analysis of EEG signals, real-time monitoring is also an important category in brain research, so that for complying with this requirement, the hair band EEG device of the present invention further employs the RF module to perform wireless signal transmission to external apparatus, such as, computer, with compatible communication interface. Moreover, based on the RF module, the external apparatus also can wirelessly control and configure the hair band EEG device, for example, start/stop operation and parameter settings, that is, the EEG signal device can have a wireless communication with the external apparatus, even during the monitoring process. Besides, since one purpose of the present invention is to maximize user mobility during EEG monitoring, it will be better to eliminate the connecting cable between the EEG monitoring device and the external apparatus, thereby the user mobility won't be sacrificed by real-time monitoring. Therefore, through employing the RF module, the reduction of wiring complexity, the enhancement of user mobility, and multiple monitoring benefits all can be achieved. Here, it should be noticed that there is no limitation to the circuit arrangement (electric components and/or modules) between the ear-worn EEG monitoring device and the external apparatus, which means the functions provided by the ear-worn EEG monitoring device is flexible, for example, the acquired EEG signals can be directly transmitted to the external apparatus after digitization, or can be processed before transmission, various situations are possible.

In various embodiments of the invention, the invention may be implemented as part of a comprehensive remote patient monitoring system, which includes the invention hair band EEG device in communication with a base receiver and server unit. The medical device data can also be transmitted to the intermediary device wirelessly using a wireless transmitter. Any suitable method of wireless communication can be used to transmit the medical device data, such as a Bluetooth connection, infrared radiation, Zigbee protocol, Wibree protocol, IEEE 802.15 protocol, IEEE 802.11 protocol, IEEE 802.16 protocol, and/or ultra-wideband (UWB) protocol. The message may also be transmitted wirelessly using any suitable wireless system, such as a wireless mobile telephony network, General Packet Radio Service (GPRS) network, wireless Local Area Network (WLAN), Global System for Mobile Communications (GSM) network, Enhanced Data rates for GSM Evolution (EDGE) network, Personal Communication Service (PCS) network, Advanced Mobile Phone System (AMPS) network, Code Division Multiple Access (CDMA) network, Wideband CDMA (W-CDMA) network, Time Division-Synchronous CDMA (TD-SCDMA) network, Universal Mobile Telecommunications System (UMTS) network, Time Division Multiple Access (TDMA) network, and/or a satellite communication network. If desired, the medical device data could be transmitted to the intermediary device using both a wired and wireless connection, such as to provide a redundant means of communication, for example. Each component may have its own power supply or a central power source may supply power to one or more of the components of the PMU 10.

Further, the invention hair band device may utilize a wireless data transmission capability to broadcast the hair band data output signal directly to a remote receiver of the external device, which could be a remote computer or a relay device. The remote receiver might also be able to broadcast information back to Head Mounted Medical Device. Bluetooth wireless technology could be utilized, which uses small broadcasting chips that can be embedded into the medical receiver to broadcast real-time or recorded data to a receiving device, which can then transmit the data to a remote location. Because Bluetooth is a two-way communication technology, information could also be transmitted from a remote location to Head Mounted Medical Device to provide the ability of a medical worker to interact with the device. Cellular technology is another means for broadcasting information to and from the recording unit. If such technology is utilized, security measures must be implemented, such as password control and encryption keys, for example, to protect the patient's medical data and to prevent unauthorized access to the recording device.

Although the hair band EEG monitoring device of the present invention can be provided with a RF module, a memory is also applicable. For example, the memory can be used to store EEG signals during the entire monitoring process, no matter the wireless real-time transmission is executed or not, for off-line analysis purpose; or the memory can be used as the buffer during wireless transmission, so that when the user is out of the receiving range of the external apparatus, the signals still can be temporarily stored for future transmission as the user is back into the receiving range; or the memory can be used to store a backup in case of poor signal quality of wireless transmission. It is further advantageous that a memory be included in the hair band EEG device for data storage, and in a preferred embodiment, the memory can be implemented as a removable memory for external access, for example, the user can just takes the memory rather than the whole device to visit the doctor for interpreting the result. For outputting the data stored in the memory, the hair band EEG device can be provided with a wired transmission interface in addition to the original RF module, such as, USB and 1394. Alternatively, the memory also can be implemented to be removable, so that data access can be executed outside the EEG monitoring device.

It will be appreciated, however, that the device may have greater utility, because, for example, the device can be used with other types of sensors (such as other types of bio-signal sensors) inside the hair band (and/or otherwise located in connection with the hair band). A variety of neurological, neuro-physiological, and effector mechanisms may be integrated in a neuro-response data collection mechanism. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly. Portable EEG with dry electrodes provide a large amount of neuro-response information. It should be recognized that other mechanisms such as Electrooculography (EOG), eye tracking, facial emotion encoding, reaction time, Functional Magnetic Resonance Imaging (fMRI) and Magnetoencephalography (MEG) can also be used in particular circumstances. The device may further include other types of multimedia capabilities, such as audio/hearing bone conduction, headphone video head mounted display (e.g., video glasses with audio speakers) and/or 3D stereoscopic.

In yet an alternate embodiment of the present invention, as exemplified in FIGS. 4A-4C, there comprises barrette EEGs comprising a locking member with two opposing parts, an inner locking member and an outer support member, to engage the strands of hair to assist in retaining invention barrette on the wearer's head. In one embodiment, the outer support and the locking member are hinged to one another for pivotal movement and can be locked in a closed position by a clasp. As such, this type of barrette is placed over the strands of hair such that the outer member is outwardly exposed and the locking member is tucked underneath the strands of hair. The locking member and outer support member are then pivoted to a closed position such that the strands of hair are clamped between the inner retaining member and the locking member. Accordingly, the outer member is maintained in an outwardly facing direction, which can serve as a fashion item that enhances the appearance of the barrette and its user. More importantly, however the barrette is adapted to position the tip of the teeth to contact the scalp of the wearer held in place by the locking mechanism of the barrette. In the more preferred embodiment, the two opposing parts are concave pieces, with the outer member snapping between two concave orientations, opposing the inner member and in parallel with the inner member. By having a locking member that is concave, the tip is oriented to be in contact with the scalp of the wearer, with the teeth engaged in this position by the hair of the wearer.

In such an embodiment, the invention barrette can have sparse electronics to monitor, record and transmit information, preferably wirelessly, to a remote patient monitoring system, or alternatively, record information and be downloaded to a remote patient monitoring system. Multiple barrette EEGs can be implemented in parallel to record information simultaneously. The EEG of the invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions. Each electrode is electrically connected to electronic circuitry that can be configured to receive signals from the electrodes and provide an output to a processor that can be mounted on the hair band or on a separate unit connected to the head band. The electronic circuitry may also be configured to perform at least some processing of the signals received from the electrodes. In some implementations electronic circuitry can be mounted on or housed within the hair band. In a preferred embodiment, the EEG signal acquisition circuitry includes a processor, an analog signal processing unit, and an A/D (analog/digital) converter, but not limited, for example, filter and amplifier also can be included therein.

The head band may or may not contain any batteries or any other power supplies. If no batteries are included the device will be powered from the external receiving device via a cable. Power can be provided by an external recording device by a power supply or converter for input into a power conditioning and distribution circuit of the hair band. If wireless technology is implemented, the device should be self-powered via a battery.

The sparse electronics and small capacity battery can be fully covered or housed by an enclosure. The electrodes on the hair band can be individually electrically connected by conductive wires to EEG recorder which can be mounted on the device or mounted nearby for wired or wireless connection. For example, An EEG recorder can include an onboard recording device, such as a flash memory, or information can be transferred wirelessly from the EEG recorder assembly to the local user interface. Power consumption is obviously a concern for wireless transmission of information.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details.

While the invention has been particularly shown and described with reference to specific embodiments thereof, it will be understood by those skilled in the art that changes in the form and details of the disclosed embodiments may be made without departing from the spirit or scope of the invention. For example, embodiments have been described herein with reference to the use of conventional landlines and cellular phones. Additionally, the various embodiments of the invention as described may be implemented in the form of software running on a general purpose computer, in the form of a specialized hardware, or combination of software and hardware. It will be understood, however, that the invention is not so limited. That is, embodiments are contemplated in which a much wider diversity of communication devices may be employed in various combinations to effect redemption.

In addition, although various advantages, aspects, and objects of the present invention have been discussed herein with reference to various embodiments, it will be understood that the scope of the invention should not be limited by reference to such advantages, aspects, and objects. Rather, the scope of the invention should be determined with reference to the appended claims.

What is claimed is:

1. An EEG hair band for recording multiple EEG signals comprising:
    a head band having a generally arcuate configuration with two ends;
    one or more non-conductive teeth that circumnavigate and extend from the head band for securing the headband to the hair of a wearer; and
    a plurality of conductive contacts positioned on the one or more non-conductive teeth and configured to contact the scalp of the wearer.

2. The EEG hair band of claim 1, wherein the head band comprises at least one reference contact and at least two additional contacts.

3. The EEG hair band of claim 2, wherein the at least one reference contact is positioned on a non-conductive tooth.

4. The EEG hair band of claim 1, wherein the head band further comprises a ground contact.

5. The EEG hair band of claim 1, further comprising at least one contact positioned on an at least one end of the head band.

6. The EEG hair band of claim 1, further comprising a battery and processor embedded within the head band, wherein the plurality of contacts are connected by one or more connections to the battery and the processor.

7. The EEG hair band of claim 6, further comprising a wireless transmitter embedded within the head band, wherein the wireless transmitter is connected by one or more connections to the processor.

8. The EEG hair band of claim 1, wherein the head band comprises a body configured to house one or more connections from the plurality of conductive contacts to additional electronic components.

9. The EEG hair band of claim 1, wherein the head band comprises one or more flexible printed circuit boards for carrying signals between the plurality of contacts and additional electronic components.

10. The EEG hair band of claim 1, wherein the head band comprises two or more non-conductive teeth.

11. The EEG hair band of claim 10, wherein at least one non-conductive tooth comprises more than one contact.

12. The EEG hair band of claim 1, wherein the one or more non-conductive teeth are removably attached to the head band.

13. The EEG hair band of claim 1, wherein the one or more non-conductive teeth comprise rounded outer surfaces.

14. The EEG hair band of claim 1, wherein the one or more non-conductive teeth are positioned parallel to the head band.

15. The EEG hair band of claim 1, wherein the one or more non-conductive teeth are arranged in one or more linear rows along the head band.

16. The EEG hair band of claim 1, wherein the one or more non-conductive teeth are polymeric.

17. The EEG hair band of claim 1, wherein the one or more non-conductive teeth comprise fabric.

18. The EEG hair band of claim 1, wherein each contact in the plurality of conductive contacts has a diameter between about 0.1 mm and about 20 mm.

19. The EEG hair band of claim 1, wherein each contact in the plurality of conductive contacts is coated with titanium oxide or silicon nitride.

* * * * *